(12) United States Patent
Ford

(10) Patent No.: US 7,402,280 B2
(45) Date of Patent: Jul. 22, 2008

(54) AUTOMATIC CRUCIBLE AND SAMPLE LOADING SYSTEM AND METHOD

(75) Inventor: Gordon C. Ford, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 591 days.

(21) Appl. No.: 10/385,547

(22) Filed: Mar. 11, 2003

(65) Prior Publication Data

US 2003/0175156 A1   Sep. 18, 2003

Related U.S. Application Data

(60) Provisional application No. 60/363,396, filed on Mar. 11, 2002.

(51) Int. Cl.
*G01N 21/00* (2006.01)
(52) U.S. Cl. ............................. 422/63; 422/64; 422/65; 422/99; 422/100; 221/93
(58) Field of Classification Search ........... 422/50–101; 436/180; 221/93
See application file for complete search history.

(56) References Cited

U.S. PATENT DOCUMENTS

| | | | |
|---|---|---|---|
| 3,899,627 A | | 8/1975 | Sitek et al. |
| 3,902,860 A | * | 9/1975 | Akai et al. ..................... 117/18 |
| 4,056,677 A | | 11/1977 | Berk et al. |
| 4,238,450 A | | 12/1980 | Bredeweg et al. |
| 4,456,580 A | * | 6/1984 | Yamada et al. ................ 422/63 |
| 4,559,201 A | | 12/1985 | Yamada et al. |
| 4,573,910 A | | 3/1986 | Bredeweg |
| 5,009,316 A | * | 4/1991 | Klein ......................... 206/443 |
| 5,395,586 A | | 3/1995 | Hemzy et al. |
| 5,441,891 A | | 8/1995 | Burkovich et al. |
| 5,585,068 A | | 12/1996 | Panetz et al. |
| 6,074,610 A | * | 6/2000 | Huang et al. .................. 422/99 |
| 6,117,391 A | | 9/2000 | Mootz et al. |
| 6,551,833 B1 | | 4/2003 | Lehtinen et al. |

* cited by examiner

*Primary Examiner*—Jill Warden
*Assistant Examiner*—Jyoti Nagpaul
(74) *Attorney, Agent, or Firm*—Price, Heneveld, Cooper, DeWitt & Litton, LLP

(57) ABSTRACT

A crucible and sample handling system and method provides a crucible-holding cartridge which is prepackaged to hold a plurality of crucibles. Upon removal of an end cap exposing an exit aperture, it is loaded onto a crucible delivery assembly which discharges individual crucibles from the cartridge onto a platform where a pick-and-place arm assembly places the crucible in a combustion furnace. Individual samples are dropped from stacked sample holding carousels onto a balance and, after weighing, are pneumatically drawn from the balance and introduced into the furnace and crucible for combustion.

6 Claims, 13 Drawing Sheets

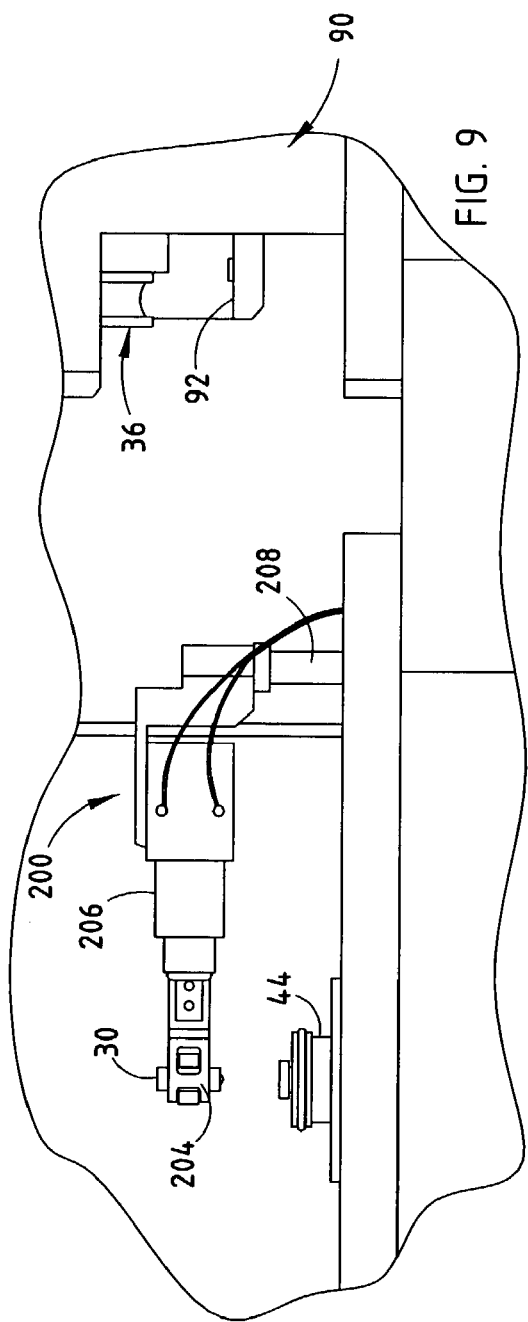
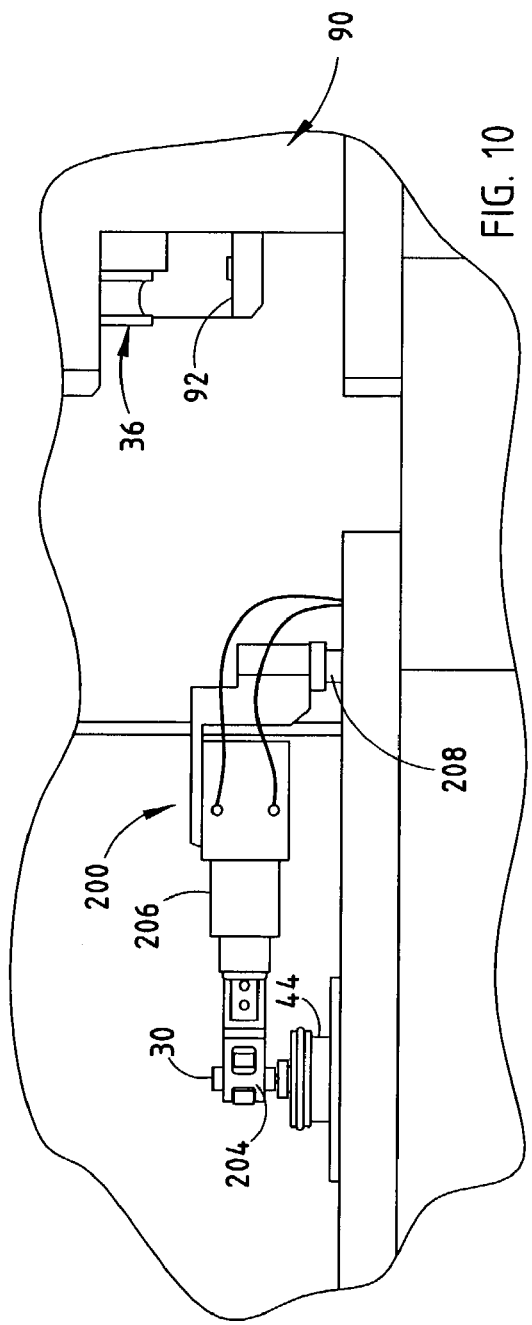

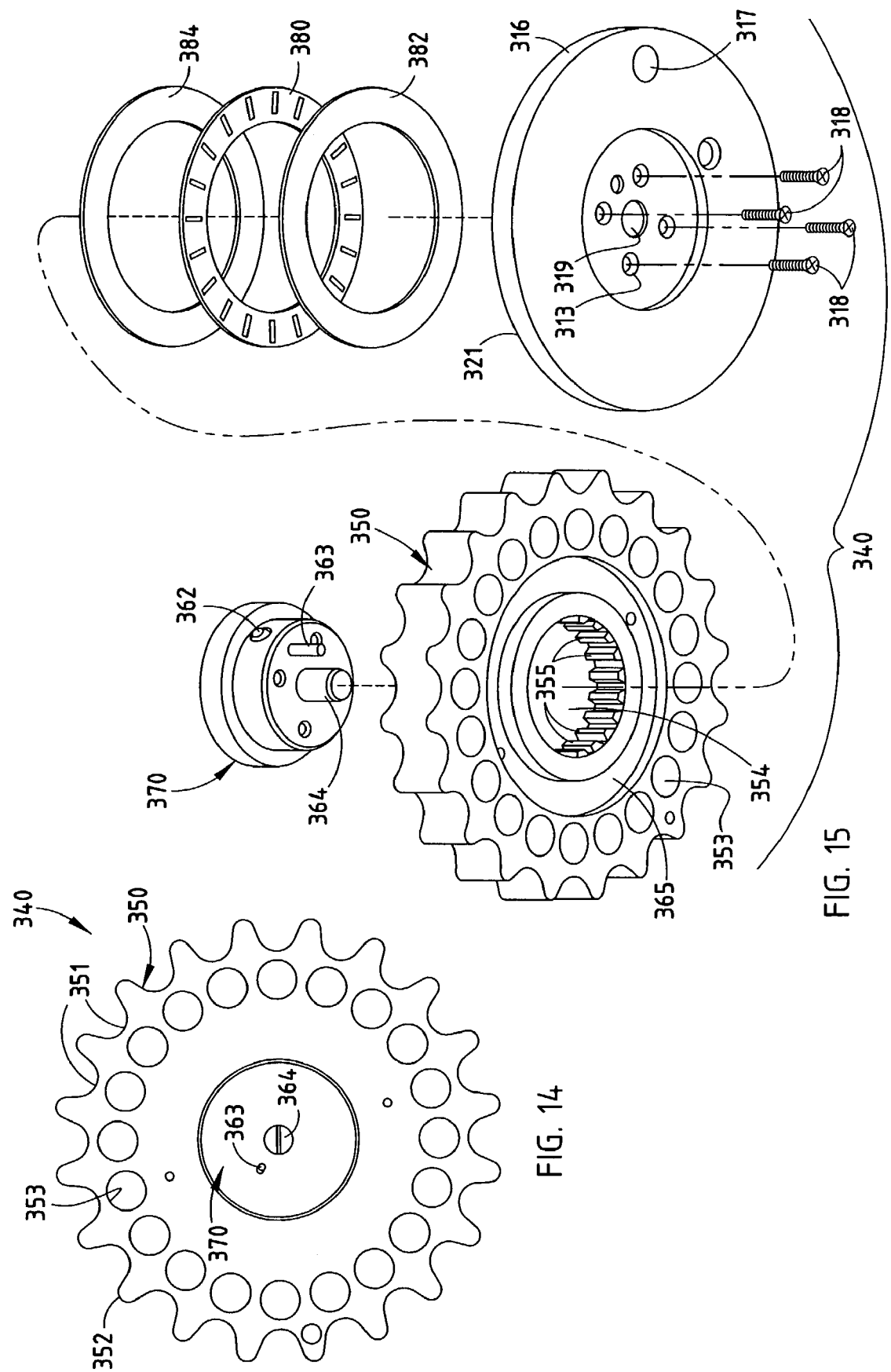

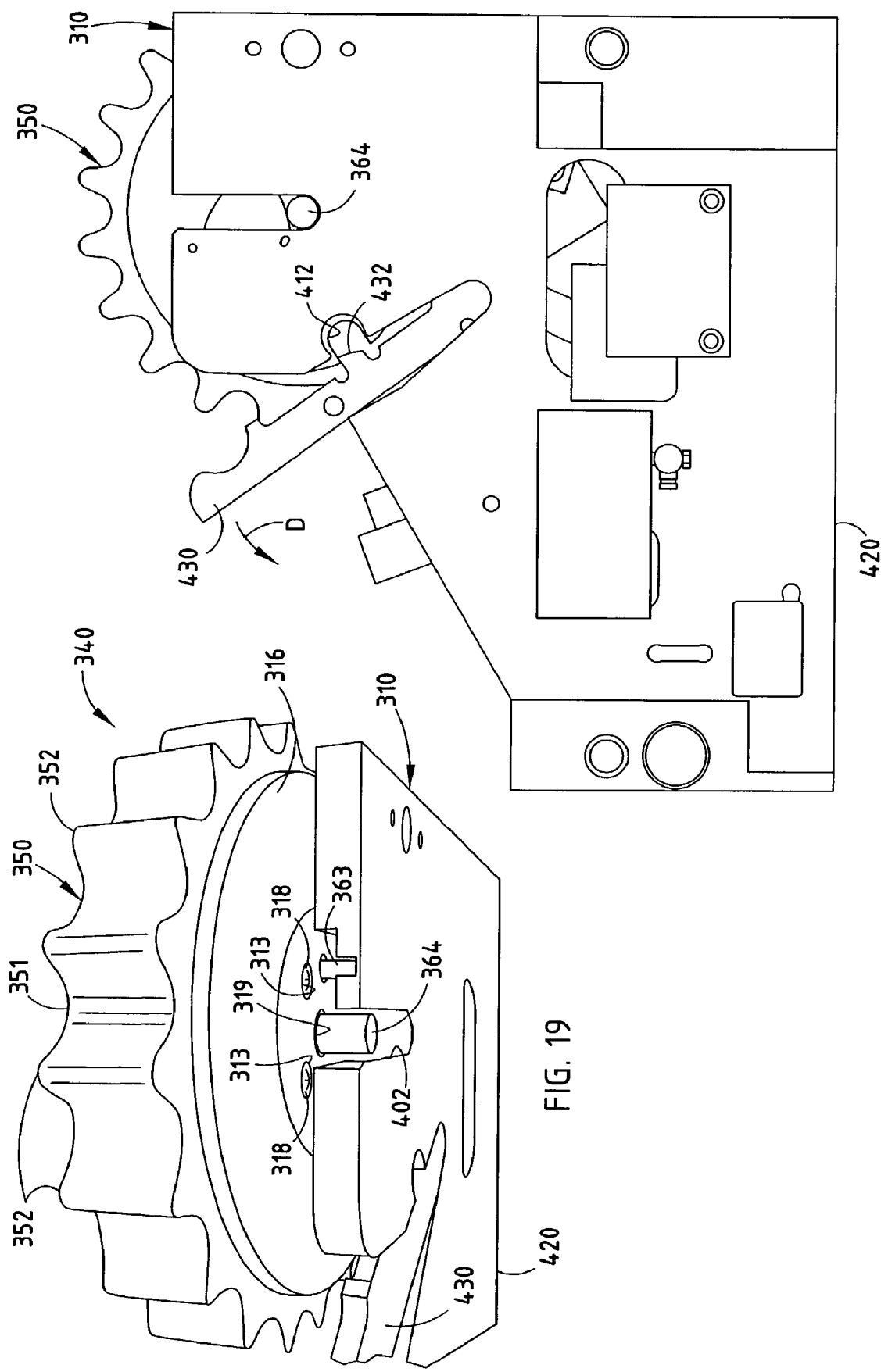

AUTOMATIC CRUCIBLE AND SAMPLE LOADING SYSTEM AND METHOD

CROSS-REFERENCE TO RELATED APPLICATIONS

This application claims priority under 35 U.S.C. § 119(e) on U.S. Provisional Application No. 60/363,396 entitled AUTOMATIC CRUCIBLE AND SAMPLE LOADING SYSTEM AND METHOD, filed on Mar. 11, 2002, by Gordon C. Ford, the entire disclosure of which is incorporated herein by reference.

BACKGROUND OF THE INVENTION

The present invention relates to a method and apparatus for packaging crucibles for use in an analytical furnace and to a system for automatically and sequentially supplying crucibles to the furnace and for automatically introducing samples into the furnace and a crucible for the combustion of the samples.

The manufacture of products such as steel require frequent sampling of the metal during its processing to assure the proper content of nitrogen and oxygen, for example. Such samples are typically combusted in crucibles in an analytical furnace. Both the samples, which frequently are pin samples, and the crucibles are typically handled manually by an analyst, requiring a significant amount of labor and time. Also, combustion furnaces reach temperatures as high as 1700° C., requiring care by the operator during the loading and unloading of sample-containing crucibles. With a resistive furnace where graphite crucibles are employed, the manual handling of crucibles results in the analyst having graphite from the crucibles rubbing off on their hands, lab coats, and some of the surrounding area. Thus, with graphite crucibles, the manual crucible handling and sample loading processes can be somewhat dirty in addition to time consuming, and can result in analytical inconsistencies due to contamination.

Efforts have been made to provide automatic loading for at least ceramic crucibles, as represented by U.S. Pat. No. 4,238,450 in which ceramic crucibles are arranged linearly and introduced upwardly into an induction furnace. Also, sample combustion boats have been the subject of auto-loading, as represented by U.S. Pat. No. 5,395,586. Although these systems provide improved handling of ceramic crucibles, the throughput provided by the systems is somewhat limited in terms of the number of crucibles which can be handled per unit time. There remains a need for a system by which crucibles can be prepackaged in bulk to the analytical laboratory, loaded into a crucible delivery assembly where the crucibles are then automatically introduced into the analytical furnace in sequence, and samples, including calibration samples, are automatically introduced into the crucible through the furnace.

SUMMARY OF THE INVENTION

The crucible and sample handling system and method of the present invention provides such a system by providing a crucible-holding cartridge which is prepackaged to hold a plurality of crucibles and is shipped to the analytical laboratory. The cartridge, upon removal of a cap exposing at least one exit aperture, is loaded onto a crucible delivery assembly which ejects individual crucibles from the cartridge onto a platform where a pick-and-place arm assembly removes the crucible from the delivery assembly and places it into a combustion furnace. The system further includes an analytical sample delivery system in which individual samples are selectively positioned onto a balance and, after weighing, are pneumatically drawn from the balance and introduced into the furnace and crucible for combustion. Both the crucible delivery assembly and sample delivery system can be automated under the control of a microprocessor such that, after a predetermined number of samples are run, the sample delivery system automatically delivers a calibration sample to the furnace for continued calibration checks of an analyzer used in association with the furnace.

The system of the present invention, therefore, provides a fully automated sample and crucible delivery assembly which eliminate the need for manual handling by an operator and one which allows a significantly increased number of samples to be run during a day. Although the invention is described in the environment of the handling of graphite crucibles for use in a resistance furnace, it is to be appreciated that the system, apparatus, and method of the present invention can be employed for handling ceramic crucibles and other objects as well.

These and other features, objects and advantages of the present invention will become apparent upon reading the following description thereof together with reference to the accompanying drawings.

BRIEF DESCRIPTION OF THE DRAWINGS

FIG. 9 is an enlarged fragmentary perspective view of the pick-and-place arm and jaws and crucible delivery assembly shown in a position transferring a crucible;

FIG. 10 is an enlarged fragmentary perspective view of a crucible being aligned above a lower electrode of the analytical furnace by the pick-and-place arm;

FIG. 14 is a top plan view of one of the sample holding carousels;

FIG. 15 is an exploded perspective view of the carousel shown in FIG. 14;

FIG. 19 is an enlarged fragmentary perspective view of a carousel during insertion into the carousel actuator; and FIG. 20 is an enlarged fragmentary bottom plan view of the carousel inserted into the actuator.

DETAILED DESCRIPTION OF THE PREFERRED EMBODIMENT

Figure 1:
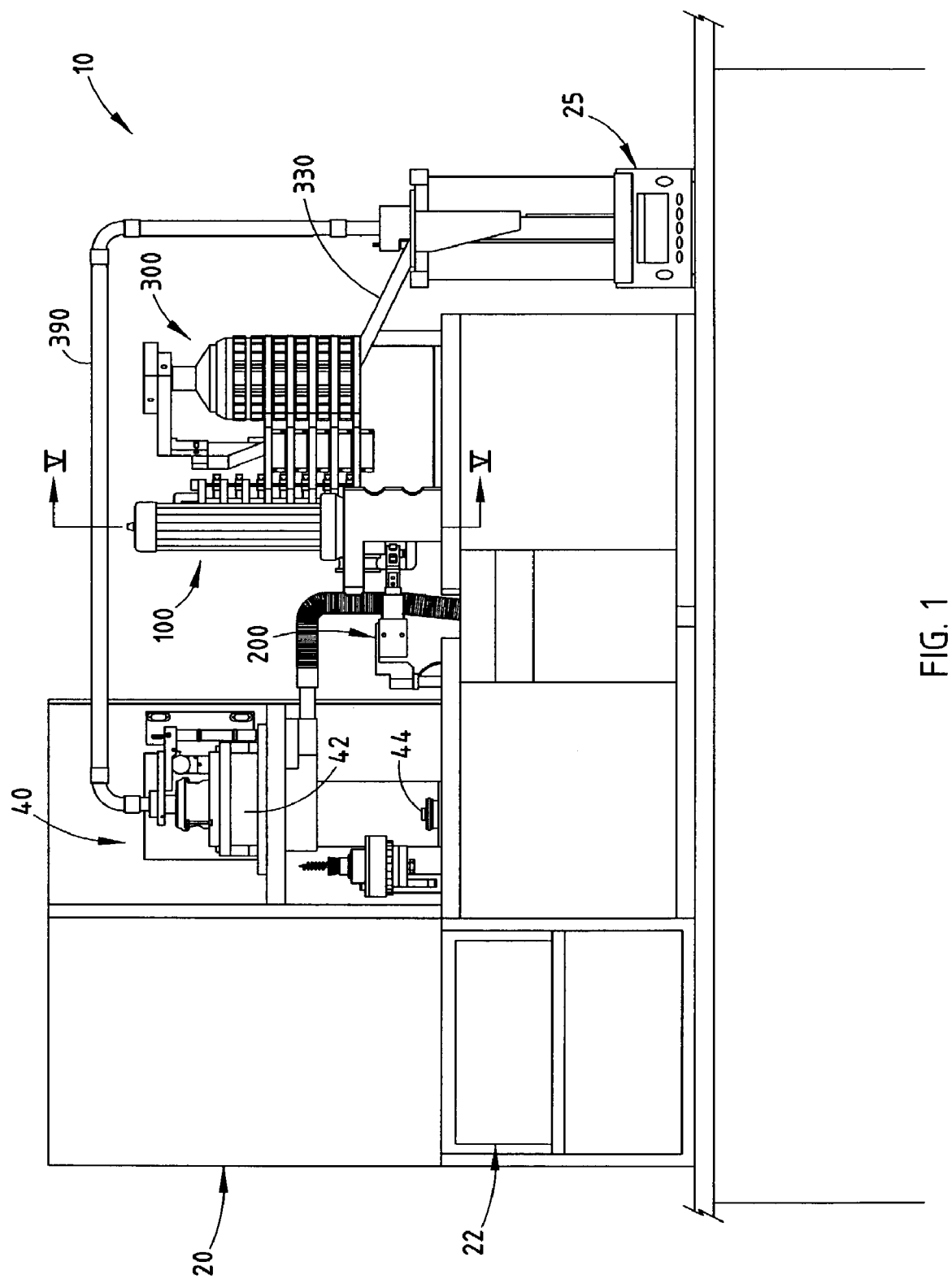
FIG. 1 is a perspective view of an analytical furnace and analyzer, including a crucible delivery assembly, a pick-and-place arm assembly, and a sample delivery system.
Figure 2:
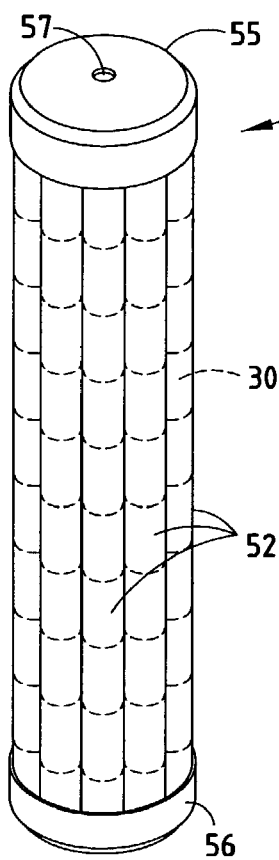
FIG. 2 is a perspective view of a loaded crucible cartridge as it is delivered to an analytical laboratory.

Referring initially to FIG. 1, there is shown an analytical system 10 embodying the crucible and sample delivery assemblies of the present invention. The analytical system comprises several major components, including an analyzer 20 which is coupled to an analytical furnace 40 which receives both crucibles, as described below, from a crucible delivery assembly 100 and samples from a sample delivery assembly 300 automatically after samples have been weighed on a balance 25. The analyzer 20, furnace 40, crucible delivery assembly 100, a pick-and-place arm assembly 200, sample delivery assembly 300, and balance 25 are all coupled to a microprocessor 22 which controls the sequence of operation to weigh samples, introduce crucibles into the furnace, introduce a sample into the furnace, combust the sample, analyze the byproducts of combustion and provide the operator with a display or printout of the results of the analysis through a printer/display (not shown).

The sample delivery assembly 300 is designed as described below to receive samples from the lab to be analyzed as well as introduce calibration samples into furnace 40 for periodically calibrating the analyzer to assure accurate analyses are being conducted. Analyzer 20 can be a thermal conductivity type analyzer, such as a TC600 which is commercially available from Leco Corporation of St. Joseph, Mich. The combustion furnace likewise can be a commercially available resistance-type furnace which includes upper and lower electrode assemblies 42 and 44, respectively. A sample is introduced by a sample delivery tube 390 (FIG. 1) through the upper electrode 42 into an awaiting crucible, such as a graphite crucible 30 (FIGS. 8-10), positioned on the lower electrode 44, as seen in FIG. 10, by the pick-and-place arm assembly 200. The furnace 40 and particularly the electrode assemblies 42, 44 can be of the type generally described in U.S. Pat. No. 4,056,677, which includes a vertically extending cylindrical passageway through the upper electrode assembly 42 to allow a sample from delivery tube 390 to be selectively dropped into the open mouth of crucible 30. Crucible 30 is, in the preferred embodiment of the invention as described herein, a graphite crucible of the type disclosed, for example, in U.S. Pat. No. 3,899,627. Having described the overall components of the system, a description first of the method of packaging crucibles including the crucible cartridge follows in connection with FIGS. 2-8, followed by a description of the operation of the crucible and sample delivery assemblies.

Figure 3:
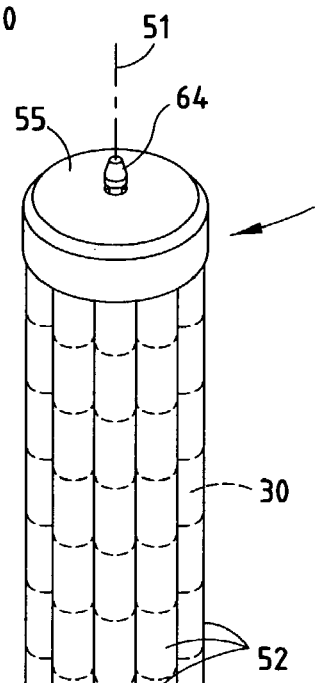
FIG. 3 is a perspective view of the crucible cassette positioned in the holder for the delivery assembly.
Figure 4:
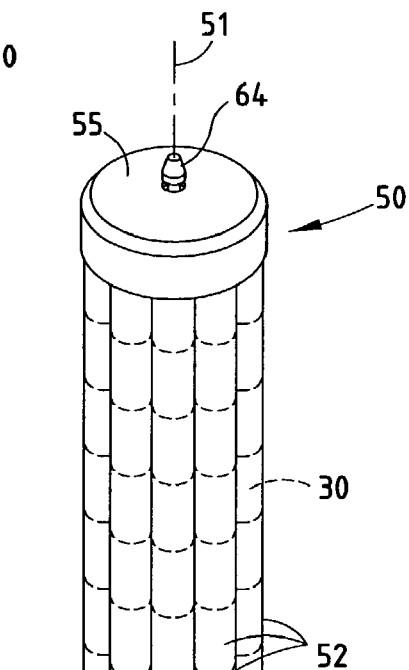
FIG. 4 is a fragmentary perspective view of the crucible delivery assembly with the cartridge and holder installed into the crucible gate actuator.
Figure 5:
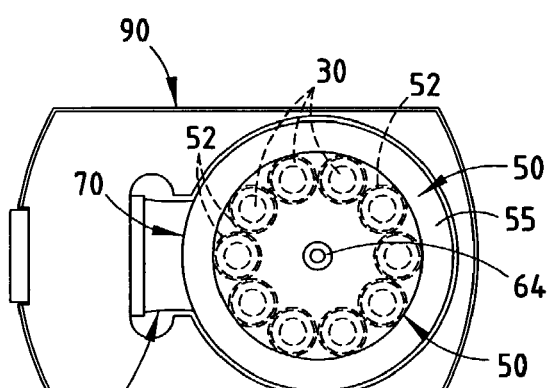
FIG. 5 is an enlarged top plan view of the crucible delivery assembly, taken in the direction of arrow V in FIG. 1.
Figures 6, 6A:
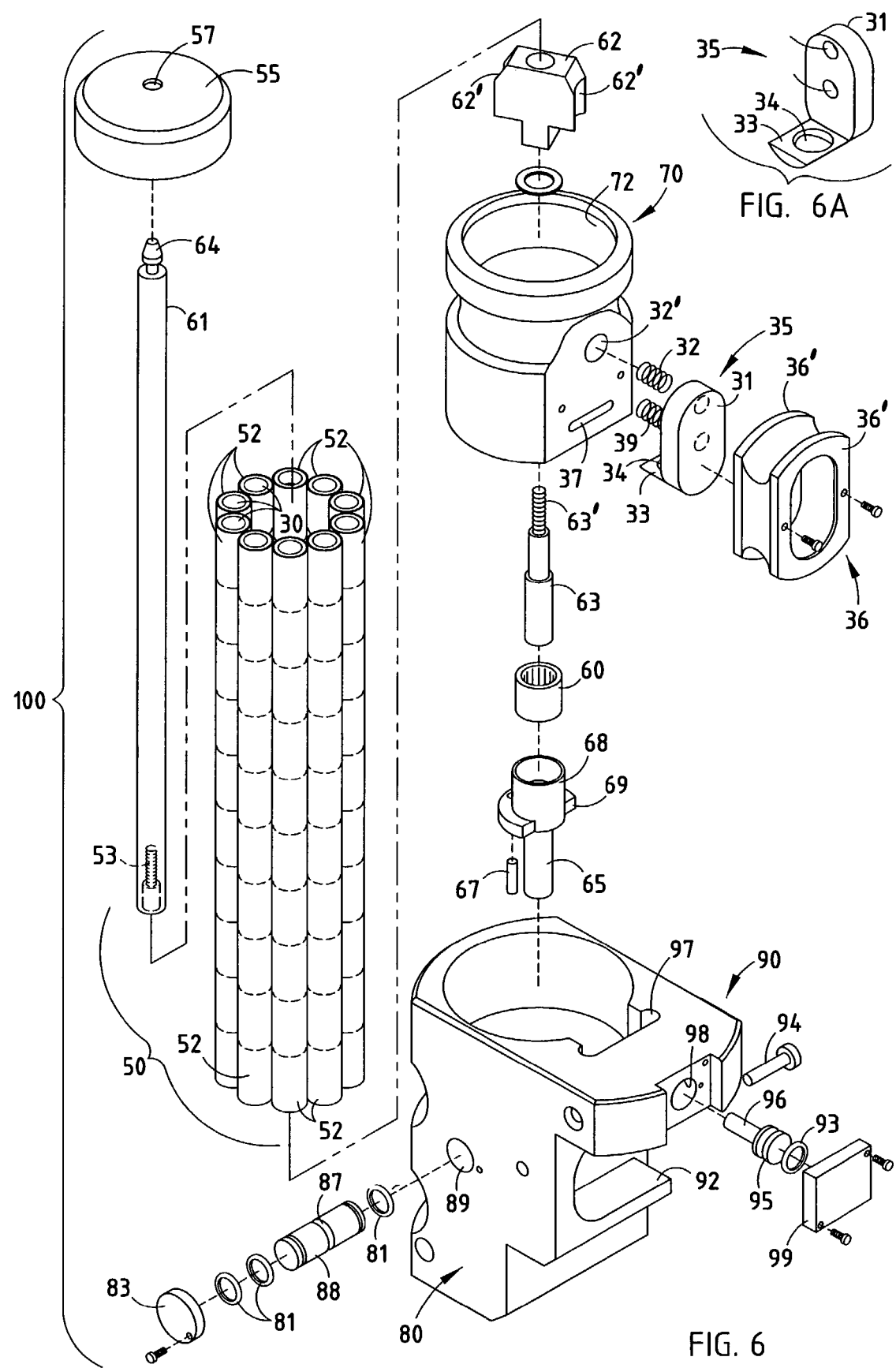
FIG. 6 is an enlarged exploded view of the crucible delivery assembly shown in FIGS. 4 and 5, shown with the exit aperture being exposed.
FIG. 6A is an enlarged perspective view of the crucible delivery gate.
Figure 7:
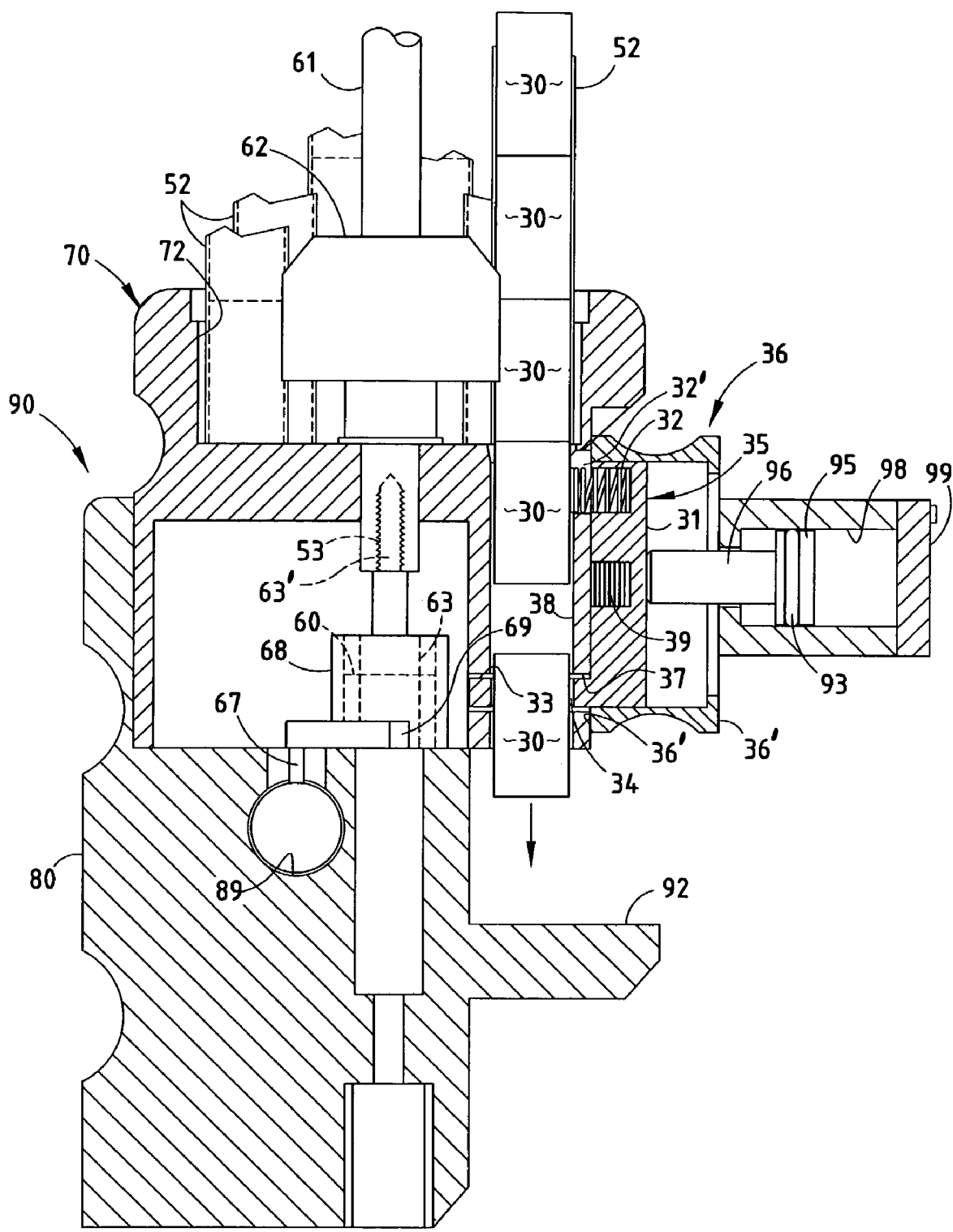
FIG. 7 is a greatly enlarged fragmentary vertical cross-sectional view of the crucible delivery assembly.
Figure 8:
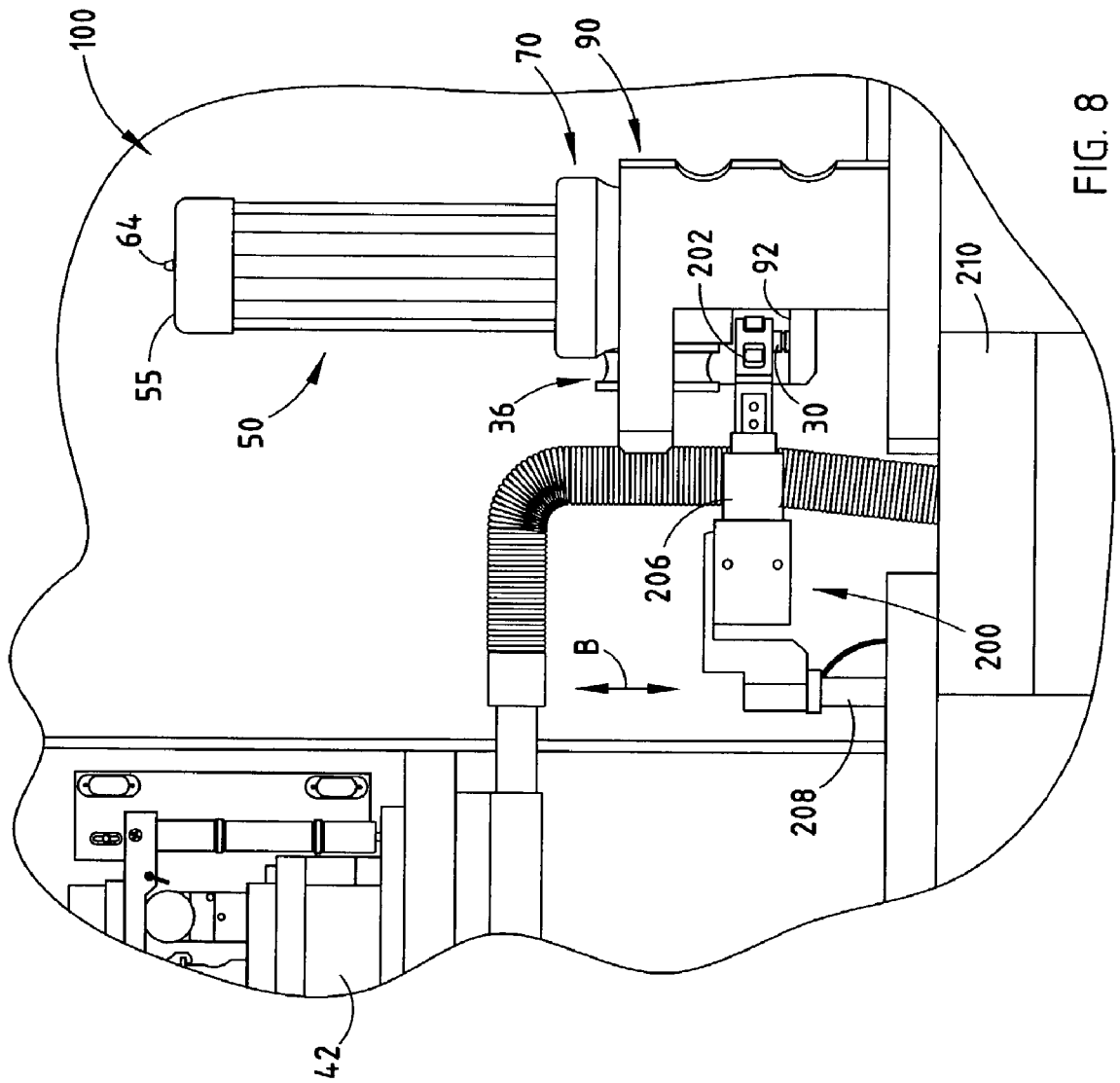
FIG. 8 is a fragmentary front elevational view of the furnace, the crucible delivery assembly including the cartridge, and the pick-and-place arm in position receiving a crucible delivered therefrom.

Referring to FIGS. 2-8, there is shown a crucible cartridge 50 which is a generally cylindrical container formed of a plurality of cylinders 52 which are clear polymeric cylinders arranged in a circular pattern, as best seen in the top view of FIG. 5, around a vertical axis of rotation 51 (FIGS. 3 and 4). The axis is coincident with a vertically extending axle 61 (FIG. 6) which extends through the center of the cylinders 52, as shown in FIG. 6, and is secured to a drive block or member 62 by means of a cylindrical drive fitting 63 having a threaded end 63' which extends within the threaded aperture 53 of axle 61 securing the axle in fixed relationship with drive member 62. Member 62 is generally rectangular having curvilinear sides 62' which are spaced to engage an inner surface of a pair of opposed cylinders 52. Such that upon rotation of drive member 62 as describe below, the generally circular cartridge 50 will rotate to position one of the cylinders 52 in alignment with a crucible delivery gate, as described below in connection with FIG. 7. Cylinders 52 have an inner diameter slightly larger than the outer diameter of the cup-shaped crucibles 30, which are packaged in the cartridge 50 by removing one of the covers 55, 56. Crucibles are slid in vertically stacked, nested relationship within each of the cylinders 52. In the preferred embodiment, ten cylinders were employed and spaced in a circular ring, as best seen in FIGS. 5 and 6, at 36° intervals. Their tangential contact points can be bonded by an acrylic adhesive or, in a preferred embodiment of the invention, a subassembly comprising the ten cylinders 52 can be integrally extruded as a single piece. An upper cap 55 includes an aperture 57 for snap-locking to a tapered locking pin 64 at the end of axle 61, as best seen in FIGS. 3, 4, and 8.

In the preferred embodiment, each cylinder 52 includes ten stacked crucibles 30 such that cartridge 50 will hold up to one hundred crucibles and, as described below, is rotated to successive 36° positions within a holder 70 by the cartridge and gate actuating assembly 90 (FIGS. 4-7) to successively position one of the cylinders in a position to drop a crucible on a platform 92 where it is picked up by the pick-and-place assembly 200, as illustrated in FIGS. 8-10, and moved to the furnace, as described below.

The crucible cartridge 50 is prepackaged, as noted above, by sliding crucibles within each of the cylinders 52 until the cartridge 50 is filled. The cap removed to fill the cartridge is then replaced and cartridge 50 shipped to the analytical laboratory for use in an instrument designed to use the packaged crucibles. The cartridge 50 is then inverted, cap 56 removed, and the crucible holder 70 placed downwardly with its pivot axle 61 placed downwardly in the open cylindrical space on the inside of the cylinders, as shown in FIG. 5, and end 64 inserted through aperture 57 to support the upper end of the axle. The drive fitting 63 secured to the axle 61 extends through a roller clutch 66 which is fitted into a drive collar 68 having a flange 69 with a drive pin 67 extending downwardly therefrom and engaging an annular groove 87 in a pneumatically actuated piston 88 fitted within an aperture 89 of crucible actuator housing 80. Suitable O-rings 81 are mounted on opposite sides of the piston 88 to seal the piston, which is pneumatically actuated in a conventional manner through an end cap 83. The linear motion of piston 88 rotates the axle 61 through the offset pin 67 which rotates the one-way roller clutch 66 driven by drive collar 68. The cylindrical post 65 of drive collar 68 fits within a blind aperture (not shown) centrally located within the cartridge-receiving aperture 72 of holder 70. The diameter of cylindrical aperture 72 is slightly greater than the outer diameter of the circle of cylinders 52, such that cartridge 50 is free to rotate within holder 70 when actuated by the cylinder 88.

The upper cap 55 of cartridge 50 may or may not include a RFID (radio frequency identification) tag. This tag coupled with an RF antenna and receiver associated with the microprocessor may be used to identify the cartridge and/or count the number of crucibles delivered from the cartridge for deactivating the crucible delivery assembly upon removal of the crucibles therefrom under the control of the microprocessor.

When cartridge 50 and cartridge holder assembly are coupled together, as seen in FIG. 3, the subassembly is then fitted within the cartridge and gate actuator 90, as seen in FIGS. 4, 5, and 7. The actuator includes the platform 92 which receives the crucible through the gate valve assembly 35, which is coupled to holder 70 and includes a piston housing 36, a piston 31, a crucible-holding spring 32 extending through an aperture 32' in the generally cylindrical holder 70. Piston 31 includes a sliding gate 33 at its lower end having an aperture 34 (FIG. 6A) having a diameter sufficient for a crucible to drop therethrough. Gate 33 extends within a slot 37 in holder 70 which aligns, as best seen in FIG. 7, with a cylindrical drop discharge chute 38 through which crucibles drop when piston 31 is actuated by conventional means to a position as shown in FIG. 7, whereupon a crucible 30 is dropped onto platform 92 from the crucible-holding cylinder 52 aligned with discharge chute 38. Spring 32, as seen in FIG. 7, holds the lowermost crucible 30' above the crucible being dropped onto the platform in position, such that a single crucible is dropped upon actuation of piston 91 by pneumatic piston 95 and push rod 96. Piston 95 includes suitable O-ring seals 93 and fits within cylinder 98 formed in block 80 and is covered by a plate 99. A pneumatic fitting 94 is coupled to a source of pneumatic pressure selectively controlled by a microprocessor controlled valve (not shown) to control piston 95. Upon deactuation of the piston 95, the return spring 39 moves gate 34 outwardly which then interferes with the discharge chute 38 while spring 32 disengages the next lowermost crucible 30', allowing it to drop onto sliding gate 33 awaiting the subsequent actuation of piston 95. When all of the crucibles of a cylinder have been expelled by gravity and the actuation of gate valve assembly 35 resulting in the alternate holding and dropping of the lowermost crucible in a cylinder 52, the microprocessor, which keeps track of the cycles of operation, sends a control signal to actuate piston 88 which rotates crucible cartridge 50 through the piston groove 87, pin 67, and roller clutch 66. The drive member 62 rotates the crucible cartridge 50 36°, positioning another cylinder 52 of crucibles 30 in position with the discharge chute 38. The piston sleeve 36 is grooved with flanges 36' to snap-fit within a mating slot 97 in the cartridge actuator block 90, as best seen in FIGS. 4-7, such that the crucible cartridge 50, once loaded onto holder 70, can then be snap-fit into the actuator 90, which effects the discharge of individual crucibles from each cylinder 52 as well as rotation of the cartridge 50 to position a new cylinder in alignment with the discharge aperture.

Each crucible 30 arriving at platform 92 are dropped into the open jaws of the awaiting pick and place arm assembly 200. The pick-and-place arm assembly 200 includes a pair of reciprocating jaws 202 and 204, as best seen in FIGS. 8-10, which are mounted to an arm 206 which, in turn, is mounted to a rotational and vertically movable post 208 which rotates between platform 92 and lower electrode 44 as described below and raises and lowers, in a direction indicated by arrow B in FIG. 8, to accommodate the different heights as necessary between the crucible delivery platform 92 and lower electrode 44 and to lower crucible 30 into precise alignment with the lower electrode 44, as seen in FIG. 10. The assembly 200 is a unit which is commercially available from Leco Corporation and is electrically and pneumatically actuated with various linear actuators under the control of microprocessor 22 to position the jaws 202, 204 in an open position as a crucible is dropped onto platform 92, thereby cradling the crucible to assure that it is captively held between the open jaws of the arm as it is delivered onto platform 92.

The sequence of transferring the crucible from the platform, as shown in FIG. 8, is shown by FIGS. 9 and 10, whereupon the raised post 208 rotates with jaws 202, 204 holding a crucible 30 and rotating to transfer the crucible from the platform 92 to the furnace 40, as seen in FIGS. 9 and 10. Post 208 then lowers to place the crucible onto electrode 44, and jaws 202, 204 are opened. The post then rotates out of the furnace area, and the upper and lower electrodes 42, 44 engage the crucible for combusting a sample therein in a known manner. The furnace then combusts the sample contained in the crucible, and the byproducts of combustion are analyzed by analyzer 20. After this, the sequence shown in FIGS. 9 and 10 is reversed and the crucible is picked from the lower electrode 44 and transported to a position where it can be dropped into a discharge bin 210 (FIG. 8). Arm 206 again moves to the position shown in FIG. 8 to await the next crucible. Having described the crucible delivery assembly 100 and its operation, a description of the sample delivery assembly 300 now follows in connection with FIGS. 11-20.

The sample delivery assembly 300 comprises a vertical stack of sample-holding carousels 340-345 which are selectively rotated to drop a crucible through aligned apertures in each carousel into a discharge tube located in alignment above the balance 25. Each sample-holding location 353 (FIGS. 14-15) in the circular disk-shaped carousels 340-345 have an identified address and the samples positioned therein accordingly are programmed such that the computer 22 (FIG. 1) knows the location of each sample to be analyzed as well as each calibration standard in the sample delivery system 300. Upon selective rotation of the carousels as described below, an identified sample from a known location will be dropped into the balance platform for weighing and subsequent delivery into furnace 40. The computer selectively controls sample delivery assembly 300 to move a carousel containing calibration standards at periodic intervals between sample analyses to assure the analyzer 20 remains calibrated and the sample analyses are accurate.

The assembly 300 comprises a base 301 (FIG. 11) which includes a plurality of upwardly extending posts, such as posts 302, 304, which receive carousel actuators 310-315 associated with an associated carousel 340-345. Each carousel, such as carousel 340 as seen in FIGS. 14 and 15, also includes a cover plate 316 with a single aperture 317 which is selectively aligned with a sample-holding aperture 353 as an associated carousel rotates with respect to its cover plate.

Rotatably mounted to actuators 310-315 by individual axles for each carousel are, in the embodiment shown, six sample-holding carousels 340-345 (although any number is possible). Each of the carousels 340-345 are substantially identical and include, as best seen by the representative carousel 340 shown in FIGS. 15 and 16, a plurality of carousel disks 350 each including sample-holding, generally cylindrical apertures 353, which are located in angular spaced relationship near the outer periphery of the carousel disks. The uppermost two carousels 344 and 345 are dedicated to samples received from input chute 319 (FIG. 11) with carousel 344 being sequentially back loaded with samples by rotating the top carousel 345 in a counterclockwise direction. Each of the carousel disks 350 include rounded peripheral ratchet teeth 352 on the outer periphery thereof which are actuated by a linear actuator mounted to the associated actuator plates 310-315, as described below, to stepwise advance the carousels incrementally, aligning one of the sample-holding apertures 353 with the aperture 317 in the corresponding cover plate 316 located below the carousel disk, as seen in FIG. 15.

Each of the carousels 340 is a separate subassembly, which is best seen in the exploded view of FIG. 15, in which one of the identical carousels 340 is shown. Carousel 340 includes the carousel disk 350 which includes a plurality of twenty openings 353 arranged at 18° intervals and which include the outer peripheral teeth 352 for engaging the actuator roller 502, as seen in FIG. 18. The carousel disk 350, as seen in FIG. 15, includes a central opening 354 with a plurality of radially inwardly extending spaced teeth 355 which selectively and releasably lock to a hub 370 having a ball plunger 362 extending radially outwardly therefrom and snap-fitting within the grooves between pairs of the teeth 355 to selectively hold a sample-holding aperture 353 in carousel disk 350 in an index-aligned position with aperture 317 aligned over the chute defined by a plurality of such aligned apertures in the remaining carousels. The hub 370 is fixedly mounted to the cover plate 316 by a plurality of screws 318. The hub including an axle 364 extends through a central aperture 319 in cover plate 316 with indexing pin 363 extending into locator aperture 313 in plate 316. The carousel disk 350 rotates between hub 370 and cover plate 316 by means of a thrust bearing 380 spanned on either side by thrust washers 382 and 384, which fit within an annular groove 365 in each carousel disk 350, such that the carousel disk can rotate with respect to hub 370 and cover plate 316. Each of the carousels 340-345 are similarly made as independent units which are releasably snap-fitted within actuators 310-315, such as one of the identical actuators 310 shown in FIGS. 16-20 and which is now described. It is noted that in FIG. 18 the carousel 350 and wheel 410 are shown in phantom form in a locked position. In FIG. 18, wheel 410 is shown in solid lines in a position to accept carousel 350.

The associated actuator, such as 310, lockably and rotatably receives the stub axle 364 of hub 370, as best seen in FIG. 19, which enters a slot 402 of one of each of the identical actuators and is lockably held therein by means of a locking wheel 410 rotatably mounted to the body 420 of actuator plate 310 by means of stub axle 408 extending through aperture 411 of locking wheel 410. Wheel 410 rotatably fits within a generally circular recess 421 in the actuator body 420 and includes an open mouthed slot 415 which receives axle 364 when wheel 410 is in an unlocked position (shown in solid lines in FIG. 18) as carousel 340 is inserted into actuator 310. The locator pin 363 of hub 370 slides within a locator slot 406 of actuator 310 and engages a flat 413 on locking wheel 410 to rotate the locking wheel in a counterclockwise direction, as indicated by arrow C in FIG. 18, as the carousel 340 is slid into actuator 310, as best seen in FIG. 19. The locking wheel 410 rotates to a locking position, as seen in FIG. 20 (and in phantom in FIG. 18), with a resilient locking bar 430 having a tooth 432 which engages a locking slot 412 in locking wheel 410 to hold the carousel 340 rotatably within the associated actuator 310. By moving the locking bar 430 in a direction indicated by arrow D in FIG. 20 manually, the wheel 410 is unlocked and free to rotate for removal and for reloading of pin standards in carousel 340 therein. Thus, the operator manually loads the carousels 340-343 and can unload all of the carousels from their associated actuators utilizing the locking wheel and latch assembly 310 shown in FIGS. 17-20.

Figure 16:
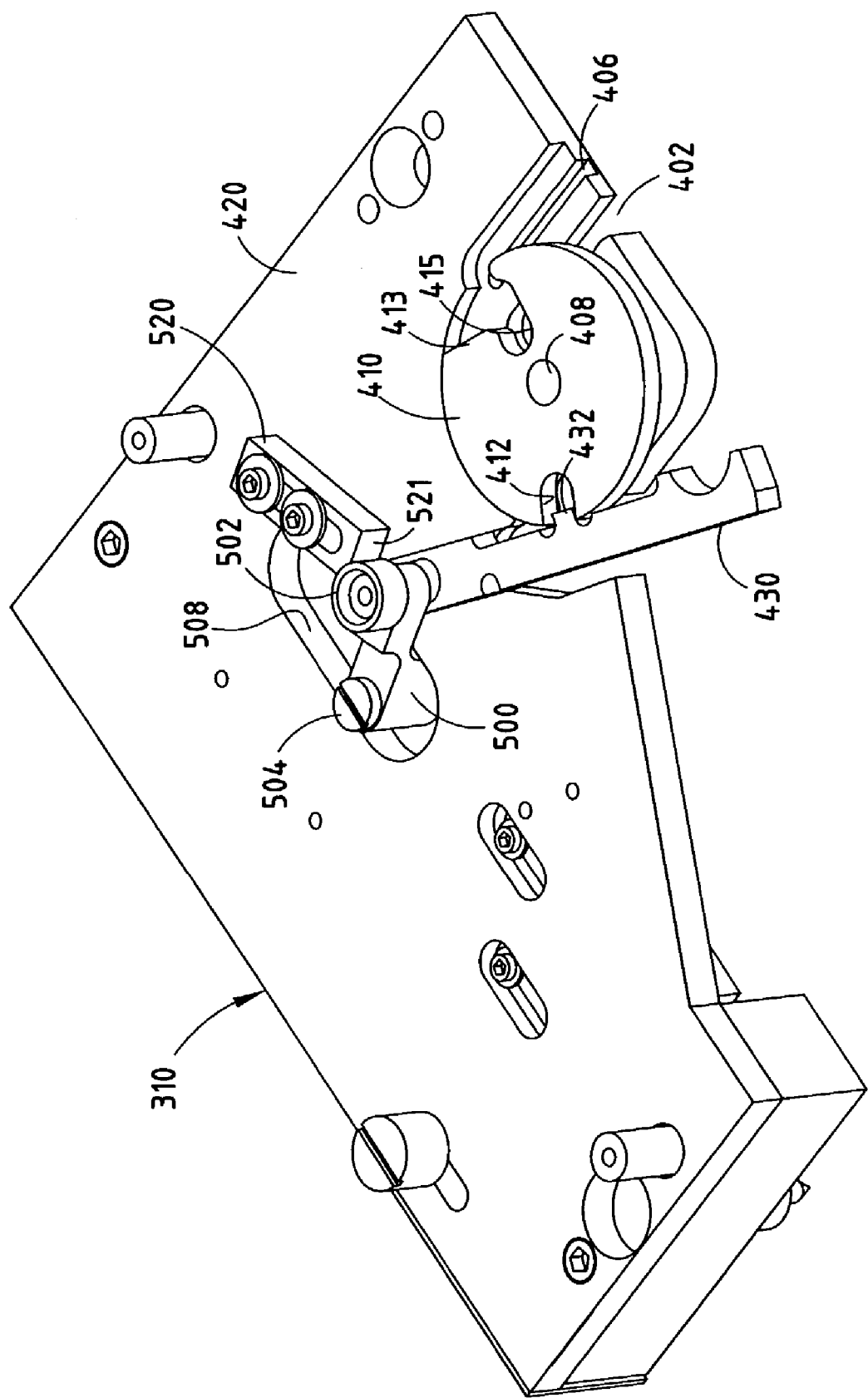
FIG. 16 is a perspective view of a carousel actuator.
Figure 17:
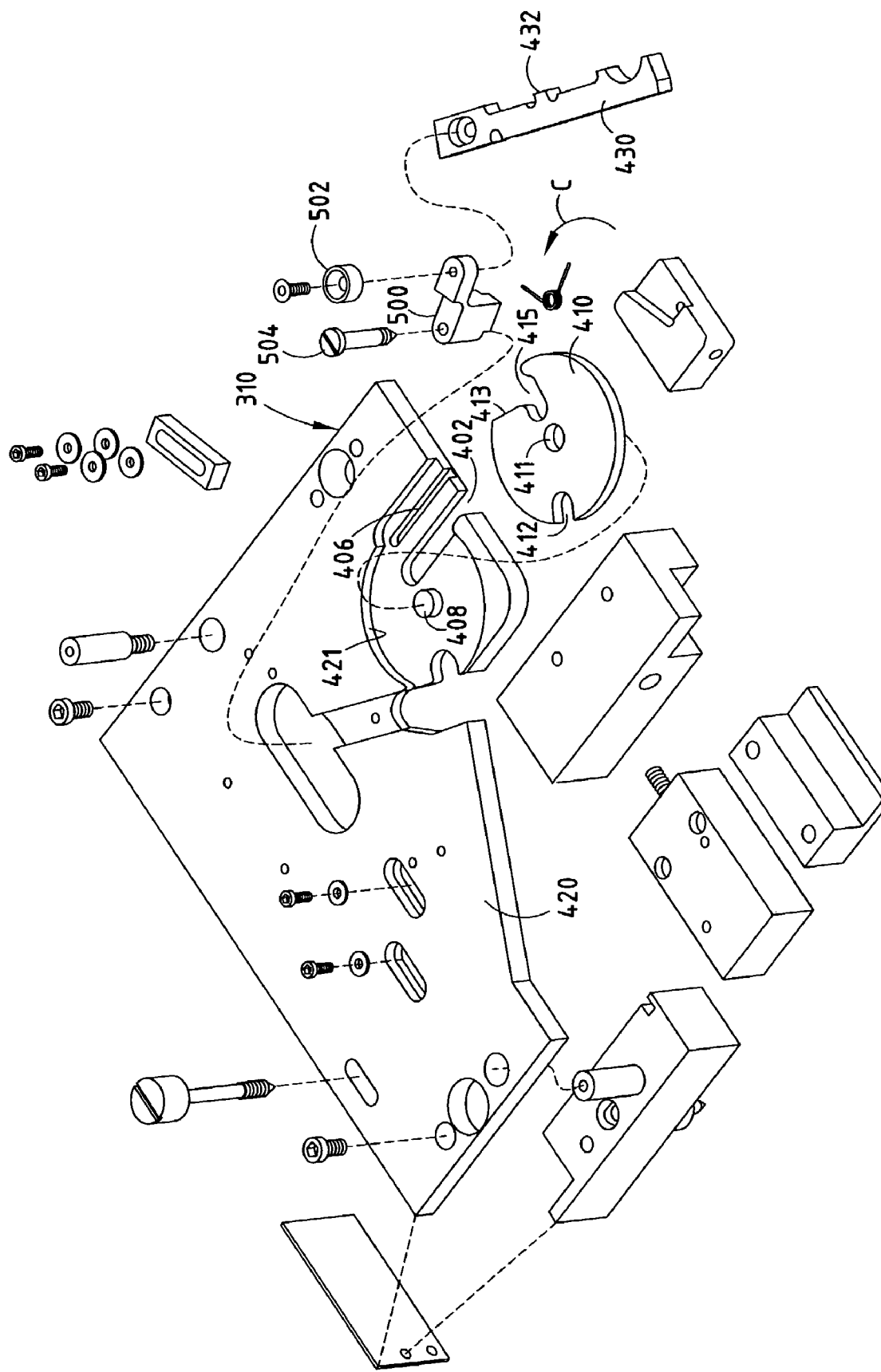
FIG. 17 is an exploded perspective view of the carousel actuator shown in FIG. 16.
Figure 18:
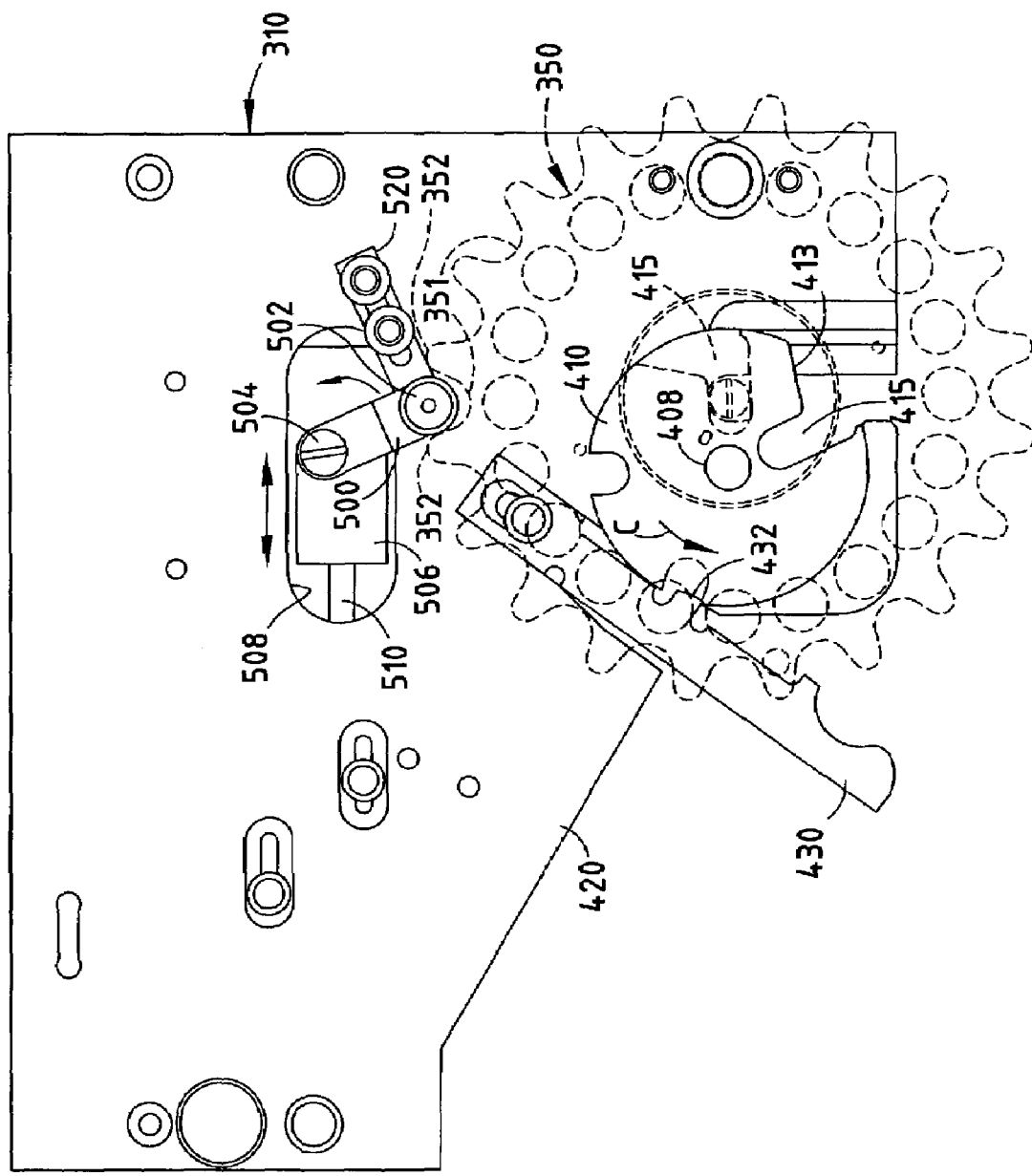
FIG. 18 is an enlarged fragmentary top plan view of the locking wheel of the carousel actuator shown in a position to admit a carousel.

Once loaded, the carousels can be stepwise advanced 18° by the actuators 310, as best seen in FIGS. 16-18. The actuator mechanism includes a roller lever 500 having a roller 502 on one end, which lever is pivotally mounted by pivot connection 504 to an arm 506 (FIG. 18) slidably mounted within slot 508 of actuator body 420. Arm 506 is coupled to the rod 510 of an pneumatic cylinder, such as cylinders 610 through 614 shown in FIG. 11. A cylinder is also associated with the top carousel but is located behind the drawing figure of FIG. 11 inasmuch as it rotates the top carousel 345 in a counterclockwise direction (i.e., opposite the remaining carousels). Upon actuation of rod 510, the roller 502 advances and engages an edge 521 (FIG. 16) of adjustable stop bar 520 set at an angle to urge the roller 502 into one of the slots 351 between teeth 352, thereby advancing the carousel disk 350 exactly 18°. Upon release of pressure of the actuating cylinder, the push plunger 362 in hub 370 has sufficient tension against the inner extending teeth 355 of carousel disk 350 to prevent the disk from moving and indexing the disk in alignment with aperture 317. Thus, each of the actuators lockably, rotatably, and removably support a carousel for advancement of the carousel in 18° increments (for the twenty aperture carousels shown) to selectively discharge either a specimen to be analyzed or a pin standard for calibrating the analyzer.

Figure 11:
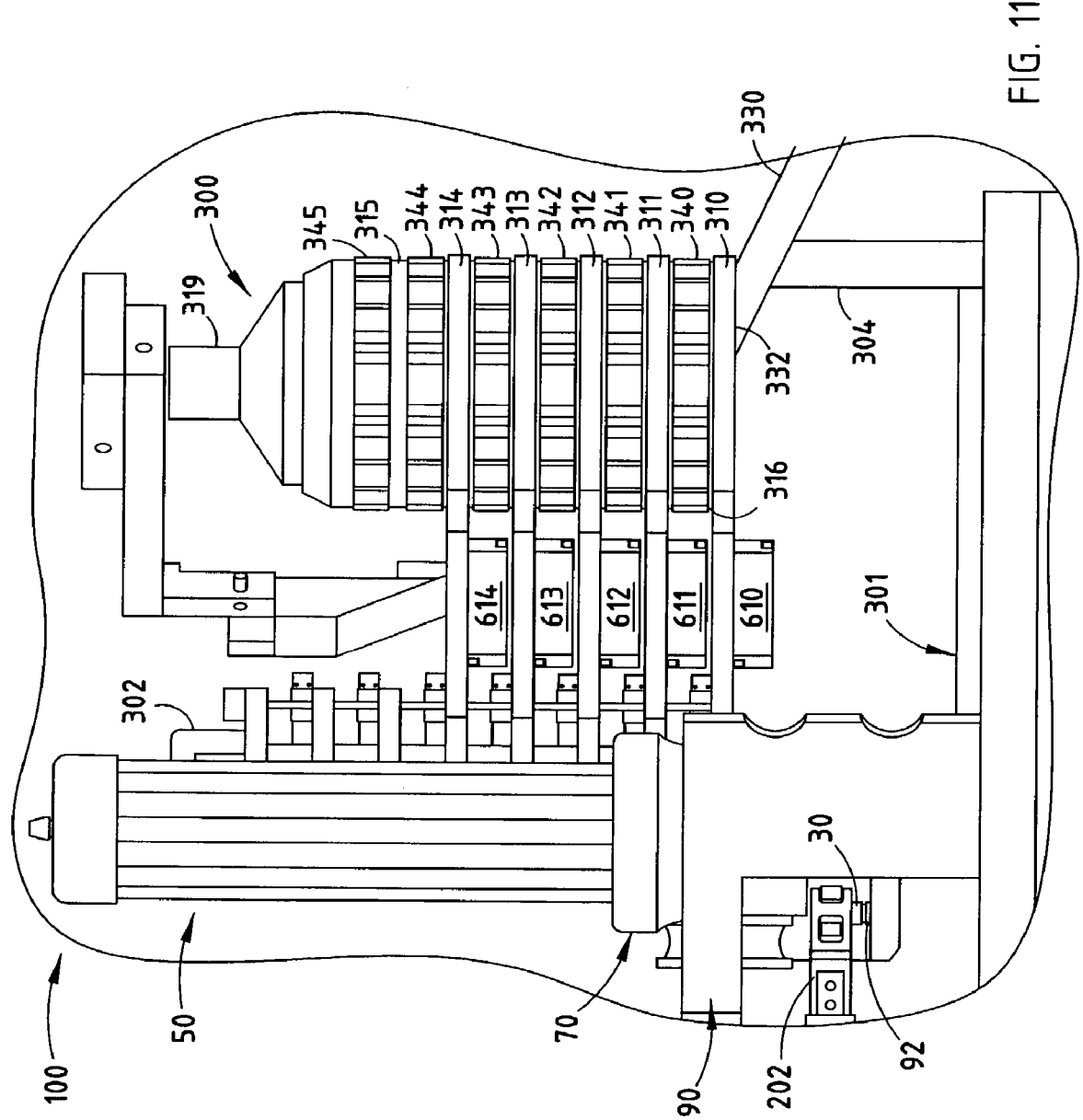
FIG. 11 is an enlarged fragmentary front elevational view of the crucible and sample delivery assemblies showing the stacked sample delivery carousels.

Carousels 340-343 are preloaded with calibration samples such that the system can be substantially continuously operated for a relatively long period of time inasmuch as the specimen samples are introduced through delivery tube 319 (FIG. 11) automatically by the laboratory conducting repeated analyses. It is noted that the carousels each include their own disk-shaped, underlying cover plates 316, such that the carousels 340-344 can be removed from the stack for loading calibration samples therein. Each of the individual plates 316 include single apertures which are aligned with one another when the carousels are vertically stacked, as seen in FIGS. 1 and 11. The apertures are all aligned with the open mouth 332 (FIG. 11) of discharge tube 330, such that as a given carousel is stepwise advanced, a sample to be analyzed or a calibration sample which is resting on the upper surface 321 (FIG. 15) of the cover plates 316 will be slidably advanced into alignment with the aperture 317 and dropped through the corresponding vertically aligned apertures 317 through the remaining plates and openings 353 in the carousel disks 350. Thus, there will exist an open chute defined by aligned apertures 353 and corresponding apertures 317 in each of cover plates 316 available for the dropping of a pin sample from any one of the carousels 340-344.

The uppermost carousel 345 is dedicated to the loading of samples and (unlike the remaining carousels) rotates in an opposite direction to drop pin samples received from the lab delivery system through a funnel-shaped delivery tube 319 into apertures 353 in underlying carousel 344 to backfill the sample-holding carousel. In order to provide continuous operation of the system, the loading carousel 345, as noted above, moves in a counterclockwise direction, while the sample delivery carousel 344 moves in the clockwise direction, such that the sample delivery carousel 344 can be continuously backfilled with new samples. Each of the carousels 340-345 has its own associated actuator 310-315 which engages the carousel teeth 352 for independently stepwise advancing a carousel selected to either drop a sample to be analyzed into the delivery chute 330 or one of the calibration samples held by carousels 340-343.

Figure 13:
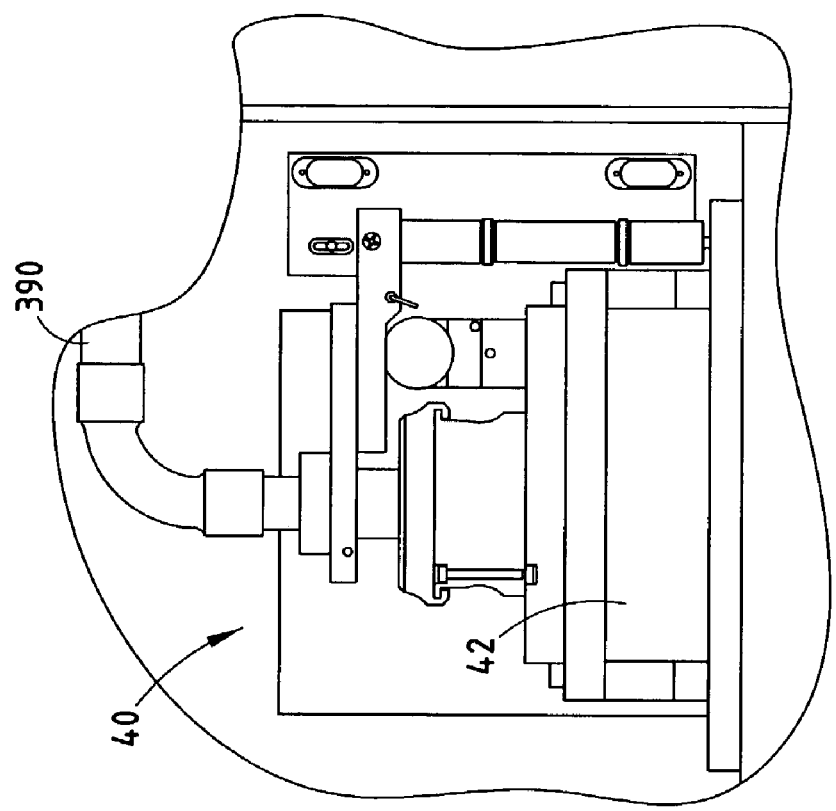
FIG. 13 is an enlarged fragmentary front elevational view of the top of the furnace as also seen in FIG. 1.
Figure 12:
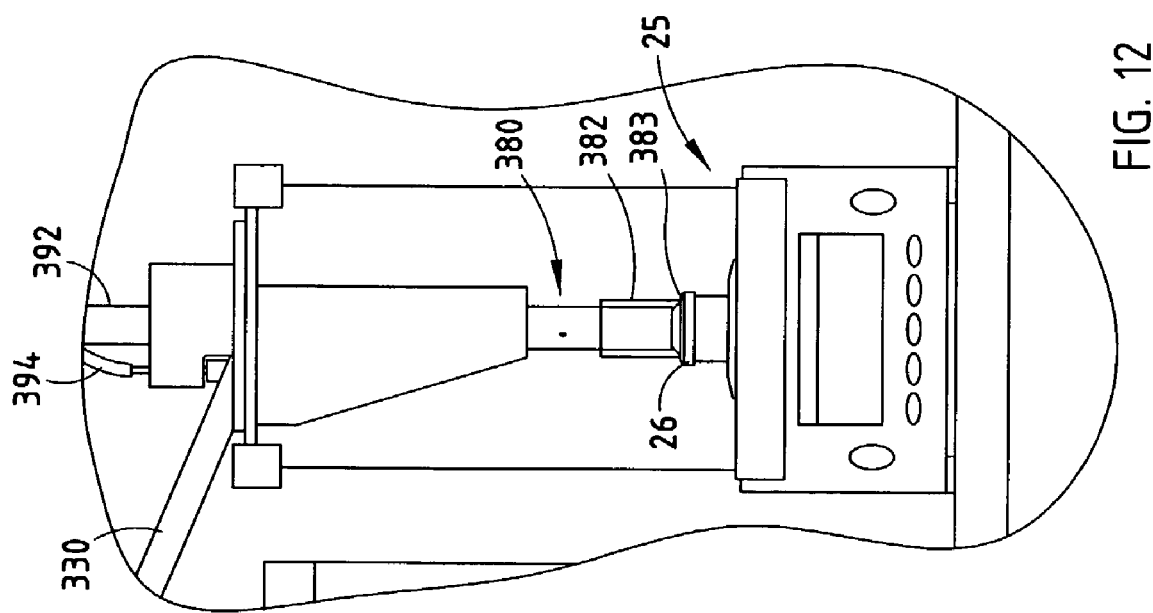
FIG. 12 is an enlarged fragmentary front elevational view of the balance showing its connection to the sample delivery system as also seen in FIG. 1.

The lower end of delivery chute 330 extends into the balance 25 and includes a movable cylindrical multiple-section telescopic tube assembly 380, which is shown in greater detail in FIG. 12. The telescopic assembly 380 includes a lowermost cylindrical tube 382, which is substantially transparent so that the operator can visually, if desired, confirm the operation of the system. The lower edge 383 of tube 382 is spaced from the balance platform 26 a distance of approximately 0.030", such that the balance only detects the weight of the sample. After weighing the sample and entering the weight in the memory of the computer 22, air pressure from tube 394 (FIG. 12) is applied to a line vac in input tube 392, which is coupled to telescopic assembly 380. The line vac is a commercially available unit and includes a venturi, such that when air pressure is applied through tube 394 for about two seconds, the line vac will provide a short duration vacuum which sucks the sample from the balance platform 26 upwardly through tube 392 into the delivery tube 390 and into the furnace 40, as seen in FIGS. 1 and 13. As noted earlier, the upper electrode assembly 42 of furnace 40 includes a sample drop mechanism which drops a sample directly into the open mouth of a crucible 30 which has been delivered to the lower electrode 44 by the crucible delivery assembly 100, as discussed above.

With both the sample delivery assembly and crucible delivery assembly of the system, automatic throughput of multiple samples can be run on a 24 hour basis by a laboratory, which can handle a throughput of up to 250 or an even greater number of samples over a 24 hour period. Each of the carousels 340-344 holds up to 19 samples which are typically one gram pin samples having a diameter of ¼" and a length of approximately 5/16". The inner diameter of the tubes 390 and 392 easily transfer the pin samples from the balance and into the analyzer furnace 40. Although the system 10 of the present invention incorporates both the sample delivery assembly and a crucible delivery assembly, it is to be understood that other analytical systems may use either one or both of these assemblies. Further, although described in the preferred embodiment as a graphite crucible delivery assembly, the crucibles can be ceramic or other material used for holding samples to be analyzed. The computer 22 will store each sample's identification as well as each sample's location in the carousels and be capable of controlling the motion of the carousels to selectively drop a calibration sample into the furnace for analysis at period intervals.

It will become apparent to those skilled in the art that various modifications to the preferred embodiment of the invention as described herein can be made without departing from the spirit or scope of the invention as defined by the appended claims.

The invention claimed is:

1. A crucible cartridge and holder assembly comprising:
a plurality of crucible-holding cylinders forming a cartridge in a circular pattern of said cylinders, each cylinder adapted to receive a plurality of crucibles therein in vertically stacked relationship;
a cover at one end of said plurality of cylinders for covering one end of said cylinders, said cover including a centrally located aperture; and
a cartridge holder for receiving an opposite end of said cylinders and including a stem extending through said aperture in said cover, said holder including a gate valve with a linearly movable sliding gate and a holding member selectively and sequentially aligned with one of said cylinders, wherein said holding member and said sliding gate of said gate valve are sequentially actuated for successively holding and then dispensing by dropping downwardly only a lowermost crucible held in said one cylinder from said cartridge.

2. The assembly as defined in claim 1 wherein said holder includes a drive member coupled to said stem and engaging at least one of said cylinders for sequentially rotating said cylinders in vertical alignment with said gate valve.

3. A crucible cartridge and holder assembly comprising:
a plurality of crucible-holding cylinders forming a cartridge in a circular pattern of said cylinders;
a plurality of analytical crucibles made of one of graphite and ceramic material and positioned in each cylinder in vertically stacked relationship; and
a cartridge holder for receiving a lower end of said cylinders, said holder including a gate valve with a linear sliding gate and a holding member selectively and sequentially aligned with one of said cylinders, wherein said holding member and said sliding gate of said gate valve are sequentially actuated for successively holding then dispensing by dropping downwardly only a lowermost crucible held in said one cylinder from said cartridge.

4. The crucible cartridge and holder assembly as defined in claim 3 wherein and further including:
a cover at one end of said plurality of cylinders for covering said one end of said cylinders, said cover including a centrally located aperture and including a stem extending through said aperture in said cover and wherein said holder includes a drive member coupled to said stem and engaging at least one of said cylinders for sequentially rotating said cylinders in vertical alignment with said sliding gate of said gate valve.

5. The crucible cartridge and holder assembly as defined in claim 3 wherein said crucible-holding cylinders are formed of a clear polymeric material.

6. The crucible cartridge and holder assembly as defined in claim 3 wherein said cartridge includes a magnetic strip encoded with crucible identification information.

* * * * *